United States Patent [19]

Löhn

[11] Patent Number: 4,902,225
[45] Date of Patent: Feb. 20, 1990

[54] DENTAL SPRAY HANDPIECE

[75] Inventor: Gerd Löhn, Biberach/Rissegg, Fed. Rep. of Germany

[73] Assignee: Kaltenbach & Voigt GmbH & Co., Biberach/Riss, Fed. Rep. of Germany

[21] Appl. No.: 249,902

[22] Filed: Sep. 27, 1988

[30] Foreign Application Priority Data

Oct. 14, 1987 [DE] Fed. Rep. of Germany ....... 3734861

[51] Int. Cl.$^4$ .............................................. A61C 17/00
[52] U.S. Cl. ........................................ 433/80; 433/29; 433/32
[58] Field of Search ...................... 433/80, 81, 85, 88, 433/29, 32

[56] References Cited

U.S. PATENT DOCUMENTS

| 4,249,899 | 2/1981 | Davis | 433/80 X |
| 4,619,612 | 10/1986 | Weber et al. | 433/29 X |
| 4,648,838 | 3/1987 | Schlacter | 433/80 X |

FOREIGN PATENT DOCUMENTS 7707816 9/1978 Fed. Rep. of Germany .
3337166 4/1985 Fed. Rep. of Germany .

Primary Examiner—Robert P. Swiatek
Assistant Examiner—Nicholas D. Lucchesi
Attorney, Agent, or Firm—Scully, Scott, Murphy & Presser

[57] ABSTRACT

A dental spray handpiece consisting of a gripping sleeve having a detachable media inlet connecting piece at one end thereof and a media discharge arrangement at its other end, media conduits extending from the media inlet connecting piece to the media discharge arrangement and discharging outwardly therefrom, thereby the media connecting piece possesses connectors for media constituted of air and water. The gripping sleeve which in its dimensions and its configuration forms a uniform basic member, is equippable as a spray handpiece with an electrical current circuit and an electrical power consumer, as well as a spray handpiece without a power consumer.

16 Claims, 4 Drawing Sheets

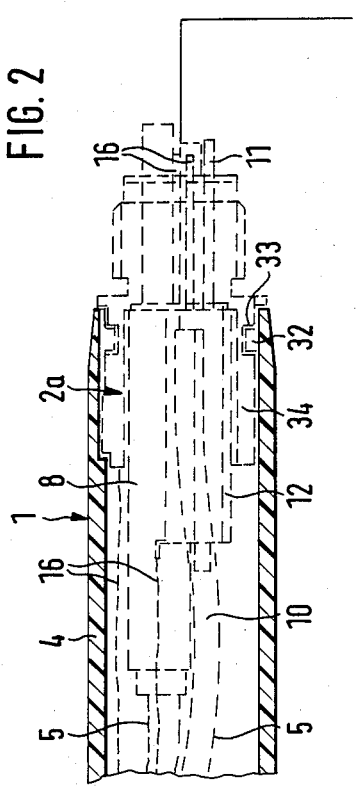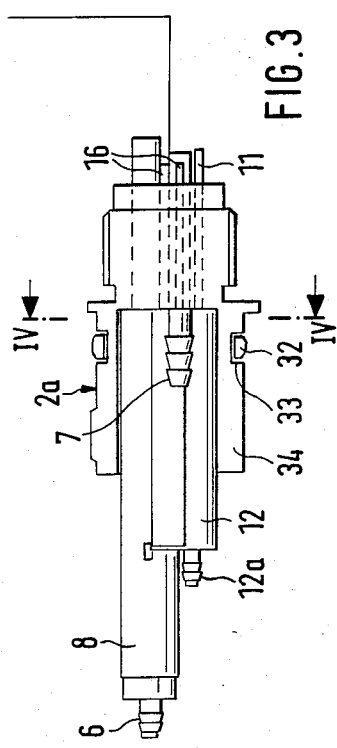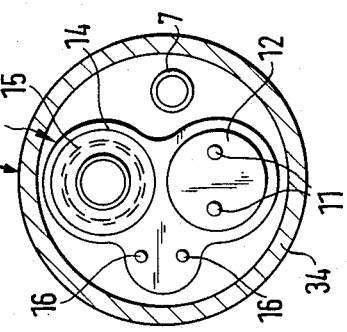

DENTAL SPRAY HANDPIECE

BACKGROUND OF THE INVENTION

1. Field of the Invention

The present invention relates to a dental spray handpiece consisting of a gripping sleeve having a detachable media inlet connecting piece at one end thereof and a media discharge arrangement at its other end, media conduits being extending from the media inlet connecting piece to the media discharge arrangement and discharging outwardly therefrom, whereby the media connecting piece possesses connectors for media constituted of air and water.

2. Discussion of the Prior Art

A spray handpiece of that type is known from the disclosure of German Laid-Open Patent Appln. No. 33 37 166. This prior art spray handpiece incorporates an electrical current circuit as a further accessory which, in this instance, serves for the supply of power to an illuminating device forming a power consumer, for the emitting of light from the region of the media discharge arrangement. Such a relatively complex spray handpiece serves mostly for use thereof by the dentist.

However, it is often adequate; for example, for use by an assistant, that a spray handpiece is utilized without a built-in current circuit; for instance, as is known from the disclosure of German Petty Patent No. 77 07 816. A simpler spray handpiece of that type, due to the elimination of the current circuit and of the power consumer, has smaller dimensions than the above-mentioned complex spray handpiece, as a consequence of which there are required two differently constructed holders for depositing of the handpieces. Moreover, because of the different dimensions for the handpieces, the necessitated manufacture of two differently constructed gripping sleeves represents a considerable demand during production and for the effected storage prior to the insertion of the media inlet connecting piece.

SUMMARY OF THE INVENTION

The invention largely eliminates the disadvantages encountered in the prior art through the provision of a dental spray handpiece of the type as considered herein, in that the latter possesses a second detachable media inlet connecting piece which is selectively insertable into the gripping sleeve and which, in addition to connections for media such as air and water, possesses a current consumer formed by an electrical heating device serving for the heating of the air, with an associated electrical current circuit. Within this context, the gripping sleeve which in its dimensions and its configuration forms a uniform basic member, is equippable as a spray handpiece with an electrical current circuit and an electrical power consumer, as well as a spray handpiece without a power consumer.

Through the advantages which are achieved by means of the invention, there can be essentially ascertained that, as a result of the two different types of media inlet connecting pieces which are associated with the gripping sleeve, in every instance there are available exteriorly identical spray handpieces for which there is required only a single type of holder. Moreover, in every instance, there need only be manufactured and stored a single type of gripping sleeve.

BRIEF DESCRIPTION OF THE DRAWINGS

Advantageous modifications and advantages of the invention may now be readily ascertained from the following detailed description thereof, taken in conjunction with the accompanying drawings which are illustrative of preferred embodiments of the invention, and in which:

FIG. 2 illustrates a longitudinal sectional view of the end of the spray handpiece which is distant from the media discharge and which is equipped with a current consumer;

FIG. 3 illustrates a side view of the media inlet connecting piece with pressure-responsive electric switch and power consumer inserted into the end of the spray handpiece pursuant to FIG. 2 distant from the media discharge;

FIG. 4 illustrates on an enlarged scale, a sectional view taken along the line IV—IV in FIG. 3;

DETAILED DESCRIPTION

Figure 1:
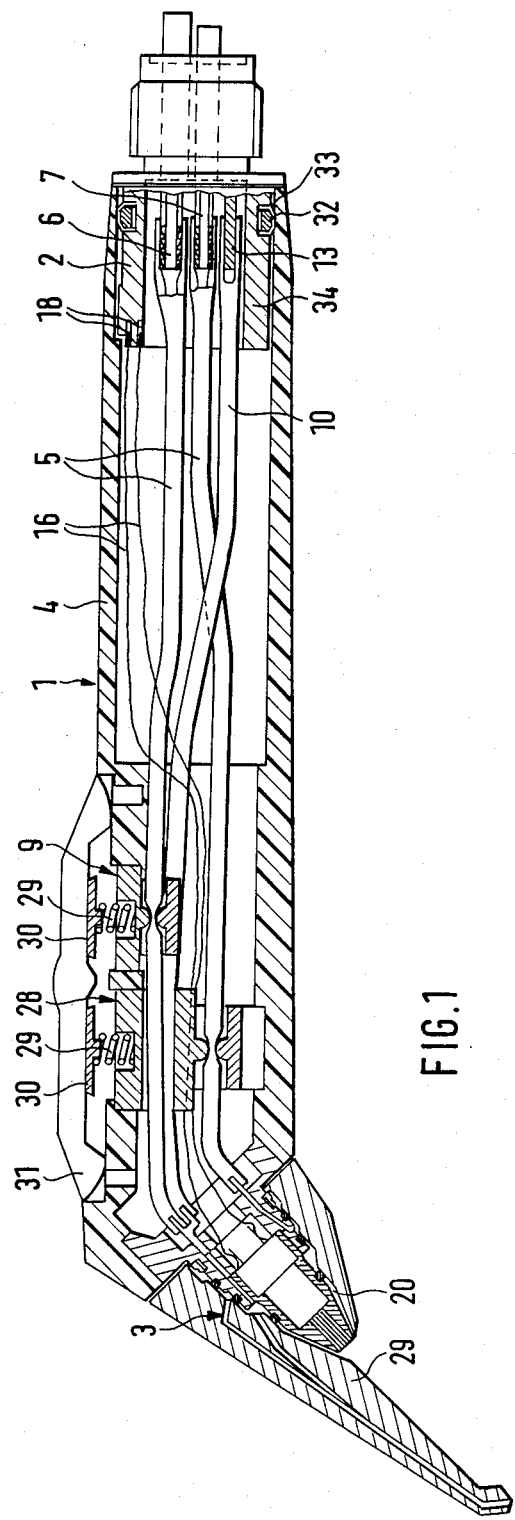
FIG. 1 illustrates a longitudinal sectional view of the inventive dental spray handpiece which is equipped without a current consumer.

The illustrated dental spray handpiece consists of a gripping sleeve 4 possessing a detachable media inlet connecting piece 2 at one end thereof, and a media discharge arrangement 3 at the other end thereof, in which sleeve there are arranged media conduits 5 leading from the media inlet connecting piece 2 to the media discharge arrangement 3 and discharging outwardly therefrom, whereby the media inlet connecting piece 2 includes connectors 6, 7 for media consisting of air and water.

The media-discharging end of the handpiece, which as shown towards the left in the drawing, is in the shape of a tip, can be constructed as a straight piece or, as illustrated, can extend in a bent or angled manner.

As a comparison between FIG. 1 and FIG. 2 illustrates, there is provided a second detachable media inlet connecting piece 2a which is selectively insertable into the gripping sleeve 4 such as the media inlet connecting piece 2, which piece 2a, besides connectors 6, 7 for the media consisting of air and water, possesses an electrical power consumer with associated current circuit 11 forming an electrical warming up of the air.

The re-equipping from the one type of handpiece to the other; in effect, from a spray handpiece with a current circuit and power consumer to a spray handpiece without a power consumer, can be performed especially simply when, pursuant to FIGS. 1 and 2, an air-shutoff valve 9 is located in the media conduit 5 for air, whereby downstream of the shutoff valve 9, a branch line 10 branches off from the media conduit 5 for air, which leads to a piezo or pressure-responsive electric switch 12 which closes a previously interrupted current circuit 11 leading to the heating device 8 in response to a pressure force, whereby the connecting piece 2 having only the connectors 6, 7 for air and water is equipped with a dummy plug 13 for the branch line 10.

In an advantageous manner, the pressure-responsive electric switch 12 hereby forms a constructional unit with the media inlet connecting piece 2a possessing the heating device 8.

The pressure-responsive electric switch 12 possesses an air central connector 12a for the branch line 10. The electrical heating device 8 consists of heating coil 15 arranged in a heating tube 14 in which is associated with the media conduit for air. The heating device 8 is hereby located upstream of the air-shutoff valve 9.

Also provided in the gripping sleeve 4 is a current circuit 16 for the operation of an incandescent lamp or lightbulb 17 which emits light from the region of the media discharge arrangement 3, whereby the connecting piece 2 possessing only the connectors 6, 7 for air and water is equipped with two blind or dummy receiving openings 18 for the connecting ends of the current circuit 6. This will also appreciably simplify the re-equipping from one type of handpiece type to the other.

The incandescent lamp is adapted to be removable, which also serves for a simple re-equipping of from one type of handpiece to the other.

In detail the arrangement is such that at the end surface of the gripping sleeve 4 towards the media discharge, a cannula 19 is detachably mounted, which possesses the media discharge arrangement 3 for air and water, whereby the incandescent lamp 17 is arranged at the end surface of the gripping sleeve 4 towards the media discharge, and the cannula 19 possesses a light-transmitting opening 20 for the light which is emitted by the incandescent lamp 17. Through this embodiment there is achieved that the cannula 19 does not possess any kind of components which conduct electric current or emit light, so as to render possible a re-equipping from one type of spray handpiece with light to a spray handpiece without light without requiring any change in or exchange of the cannula 19.

Thereby, the incandescent lamp is arranged within a covering cap 21 which projects from the end surface of the gripping sleeve towards the media discharge, and which concurrently provides a plug connector extension for the cannula 19, the end 22 of which distant from the handpiece is permeable to light. The cannula 19 is hereby rotatably mounted on the covering cap 21 which forms the plug connector extension.

In order to facilitate the permeability for light, the end 22 of the covering cap 21 distant from the handpiece possesses a light-transmitting opening 23, in which there is arranged a light-conductor 24; for example, a glass insert.

The covering cap 21 has the end 25 thereof facing towards the end piece inserted into a receiving sleeve 26 arranged at the end surface of the gripping sleeve 4 towards the media discharge, and is latched therein with the aid of locking projections 27, which also serves for a simple re-equipping of from one type of handpiece to another. The transfer of media (air, water) from the receiving sleeve 26 into the media discharge passageways 3a of the cannula 19 can be carried out with the aid of a known per se annular passageway arrangement.

Figure 5:
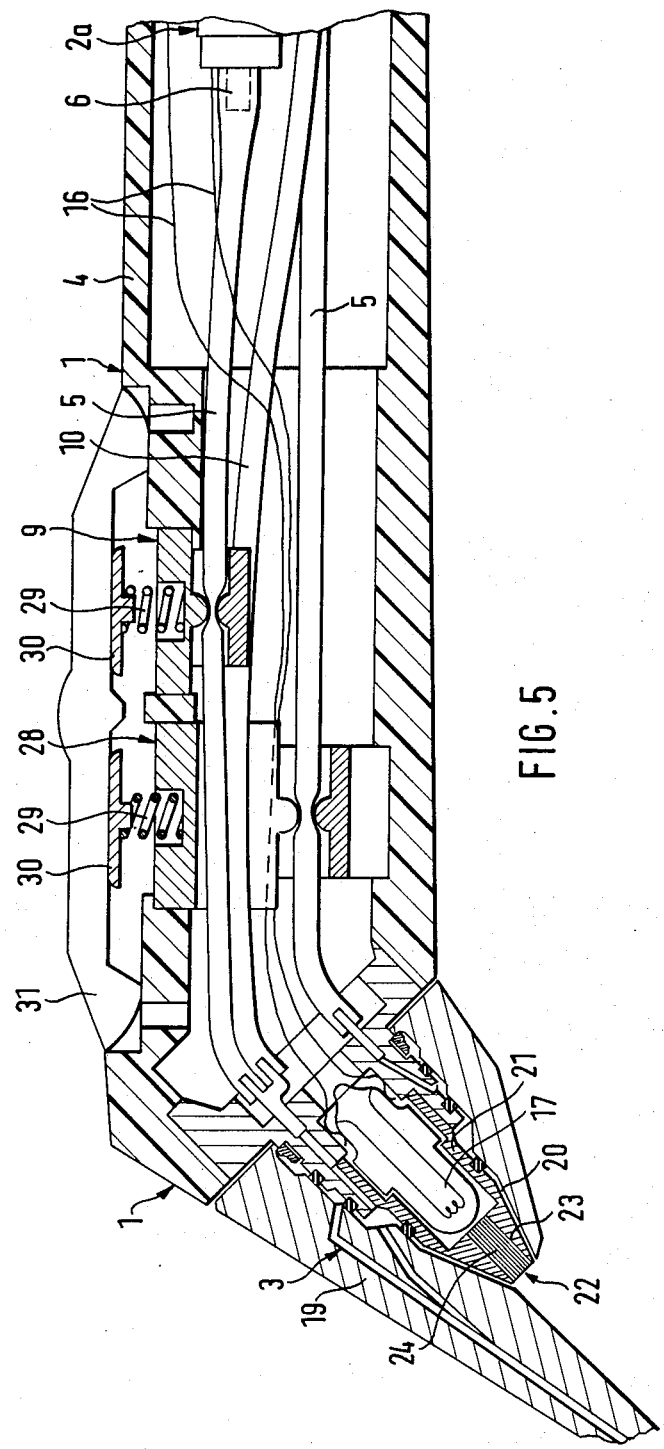
FIG. 5 illustrates the continuation of the end of the spray handpiece which is distant from the media discharge end as shown in FIG. 2, with the end towards the media discharge being shown in a longitudinal section on an enlarged scale.
Figure 6:
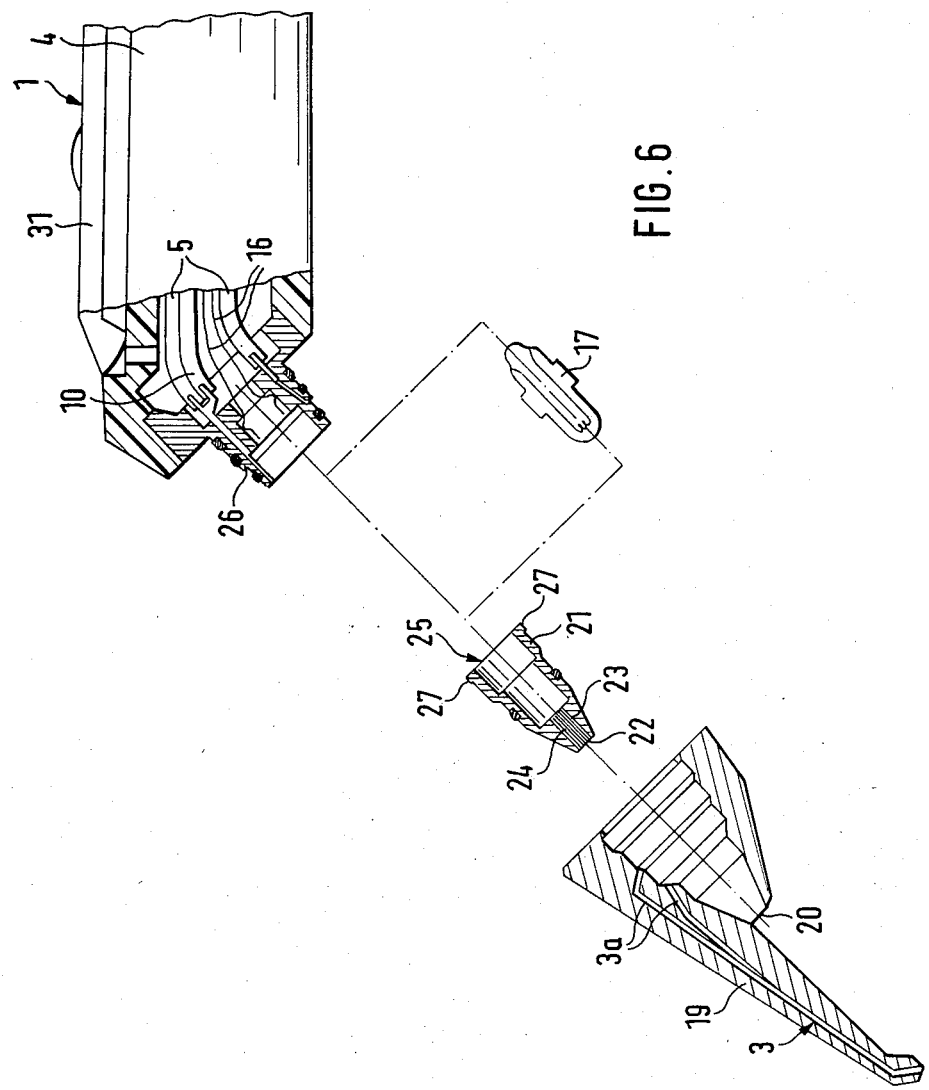
FIG. 6 illustrates a longitudinal sectional view of the end of the spray handpiece towards the media discharge side in its disassembled condition.

As is illustrated in FIG. 1 and 5, a water-shutoff valve 28 is located in the media conduit 5 for water. The air-shutoff valve 9 and the water-shutoff valve 28 are arranged behind each other along a jacket line or generatrix on the circumference of the gripping sleeve.

The two shutoff valves 9, 28, each possess a pushbutton 30 which is depressable, against the action of a return spring 29, from the closed position into the open position, whereby the two pushbuttons 30 are covered by an elastic covering 31, for example, constituted of rubber, plastic or the like. The media connecting pieces 2, 2a each possess an external clamping ring 32, which serves for the purpose of providing a clamping engagement of the connecting pieces 2, 2a in the gripping sleeve 4. In detail the construction is such that the clamping rings 32 are arranged in an external groove 33 in a coupling sleeve 34 for the connecting pieces 2, 2a.

What is claimed is:

1. Dental spray handpiece comprising a gripping sleeve having a detachable and interchangeable media inlet connecting piece insertable at one end thereof and a media discharge arrangement at the other end thereof; air and water media conduits in said gripping sleeve leading from the media inlet connecting piece to the media discharge arrangement, said media connecting piece including connectors for media consisting of air and water; an air-shutoff valve for air being arranged in the media conduit for air, a branch line for air in said connecting piece branching off from the media conduit for air downstream of said air-shutoff valve, and said connecting piece possessing the connectors for air and water being provided with a dummy plug for sealing off said branch air line.

2. Dental spray handpiece comprising a gripping sleeve having a detachable and interchangeable media inlet connecting piece insertable at one end thereof and a media discharge arrangement at the other end thereof; air and water media conduits in said gripping sleeve leading from the media inlet connecting piece to the media discharge arrangement, said media connecting piece including connectors for media consisting of air and water; said media connecting piece including an electrical power consumer with an associated current circuit constituting electrical heating means for heating of the air; an air-shutoff valve for air being arranged in the media conduit for air, a branch line for air in said connecting piece branching off from the media conduit for air downstream of said air-shutoff valve, said branch line leading to a pressure-responsive electric switch for closing a previously interrupted current circuit communicating with the heating means in response to the imposition of a pressure force.

3. Spray handpiece as claimed in claim 2, wherein the pressure-responsive electric switch is constructed unitarily with the connecting piece possessing said heating means; and said switch includes an air control connector for the branch line.

4. Spray handpiece as claimed in claim 2, wherein said electrical heating means includes a heat coil arranged in a heating tube associated with the media conduit for air.

5. Spray handpiece as claimed in claim 2, wherein said heating means is located upstream of the air-shutoff valve.

6. Spray handpiece as claimed in claim 1 or 2, wherein a current circuit is arranged in said gripping sleeve for the operation of an incandescent lamp emitting light from the region of the media discharge arrangement, said connecting piece possessing the connections for air and water being provided with two blind receiving openings for the connector ends of the current circuit.

7. Spray handpiece as claimed in claim 6, wherein said incandescent lamp is removable.

8. Spray handpiece as claimed in claim 7, wherein a cannula is detachably mounted at the end surface of the gripping sleeve towards the media discharge for air and water, said incandescent lamp being arranged at the end surface of the gripping sleeve towards the media discharge, and said cannula including a light-transmitting opening for the light emitted from said incandescent lamp.

9. Spray handpiece as claimed in claim 8, wherein said incandescent lamp is arranged within a detachable covering cap projecting from the end surface of the gripping sleeve towards the media discharge, said cap concurrently forming a plug connector extension for the cannula, with the cap having a light-permeable end distant from the handpiece.

10. Spray handpiece as claimed in claim 9, wherein said cannula is rotatably mounted on the covering cap forming the plug connector extension.

11. Spray handpiece as claimed in claim 9, wherein the end of the covering cap distant from the handpiece possesses a light-transmissive opening, with a light-conductor being located in said opening.

12. Spray handpiece as claimed in claim 9, wherein the end of said covering cap towards the handpiece is inserted into a receiving sleeve arranged on the end surface of the gripping sleeve towards the media discharge, and locking projections for locking said cap therein.

13. Spray handpiece as claimed in claim 1 or 2, wherein a water-shutoff valve is arranged in the media conduit for water.

14. Spray handpiece as claimed in claim 13, wherein said air-shutoff valve and said water-shutoff valve are arranged behind each other along a jacket line on the circumference of the gripping sleeve.

15. Spray handpiece as claimed in claim 13, wherein said two shutoff valves each includes a pushbutton depressable against the action of a return spring from a closed position into an open position, said two pushbuttons being covered by an elastic covering.

16. Spray handpiece as claimed in claim 1 or 2, wherein said media connecting piece includes an external clamping ring to provide a clamping seat in the gripping sleeve.

* * * * *